(12) United States Patent
Gao et al.

(10) Patent No.: US 6,300,435 B1
(45) Date of Patent: Oct. 9, 2001

(54) IRON OLEFIN COPOLYMERIZATION CATALYST

(75) Inventors: Xiaoliang Gao; Qinyan Wang; Matthew Gerald Kowalchuk, all of Calgary (CA)

(73) Assignee: Nova Chemical (International) S.A., Calgary (CA)

( * ) Notice: Subject to any disclaimer, the term of this patent is extended or adjusted under 35 U.S.C. 154(b) by 0 days.

(21) Appl. No.: 09/466,510

(22) Filed: Dec. 17, 1999

(51) Int. Cl.$^7$ ................................ C08F 4/14; C08F 4/44
(52) U.S. Cl. ................. 526/133; 526/134; 526/172; 526/348.6; 526/352; 502/162; 556/13; 556/138
(58) Field of Search ....................... 526/172, 133, 526/134, 348.6, 352; 502/162; 556/13, 138

(56) References Cited

U.S. PATENT DOCUMENTS

| | | |
|---|---|---|
| 5,557,023 | 9/1996 | Somogyvari et al. . |
| 5,589,555 | 12/1996 | Zboril et al. . |
| 6,121,181 * | 9/2000 | Etherton et al. ................ 502/103 |

FOREIGN PATENT DOCUMENTS

WO98/27124    6/1998    (WO) .

OTHER PUBLICATIONS

Riese et al., Phosphoraneiminato Complexes of Ag(1), Mn(II), and Co(II), Lecture 060 at conference held in Toronto, Ontario, Canada from May 30 to Jun. 2, 1999.*

I Mhoff et al, "Stabilization of Rhodium . . . " Organometallics 1991, 10, 1421–1431.

Avis et al, "Selective Formation of Four Membered Mettalacyclic Pt–N–P–C Compounds . . . ", Inorganic Chem. 1995, 34, 4092–4105.

Avis et al, "Reactions of Bis(Iminophosphoranes with Palladium . . . ", J. Organomet. Chem. 527 (1997) 263–276.

Avis et al, "Monodentate and Bidentate α–N,α–N' Coordination of 1,1–Bis(N–p–Tolylimino)Diphenylphosphoranyl)Ethane . . . " Inorg. Chem 1996, 35 1518–1528.

Ong et al "The Development of Diimine and Phosphinimine Ligand System" 1999.

Lecture 60 Kiese et al "Phoshoraneiminate Complexe . . . ".

Kiese, et al Phosphoraneiminato Cluster of Iron Z. Anorg. Allg. Chem. 625, 746–754 1999.

U. Riese et al., Phosphoraneiminato Complexes of Ag(I), Mn(II), and Co(II), Lecture 060 at conference held in Toronto, Ontario, Canada from May 30 to Jun. 2, 1999.

* cited by examiner

*Primary Examiner*—David W. Wu
*Assistant Examiner*—R. Harlan
(74) *Attorney, Agent, or Firm*—Kenneth H. Johnson

(57) ABSTRACT

Olefin Co- or homopolymers having a good molecular weight and short chain branching may be prepared in the presence of Group 8, 9 or 10 phosphinimine complex other than nickel.

88 Claims, No Drawings

IRON OLEFIN COPOLYMERIZATION CATALYST

FIELD OF THE INVENTION

The present invention relates to late transition metal complexes, a process for their preparation and their use in the polymerization of olefins.

BACKGROUND OF THE INVENTION

The papers Organometallics, 10, 1421–1431, 1991; J. Organomet. Chem., 527(1–2), 263–276, 1997; Inorg. Chem., 35(6), 1518–28, 1996; and Inorg. Chem., 34(16), 4092–4105 (English) 1995 report the reaction of bis(iminophosphoranyl) methane (BIPM) which are typically aryl substituted on the phosphorus atom and the nitrogen with group VIII metal halides (chlorides) further comprising at two weakly coordinating ligands (L) such as nitriles or cyclooctadiene, afforded several products depending on the reaction time, type of ligand or nature of the metal. The product could be a N-C chelating type product or a N-N chelating type product.

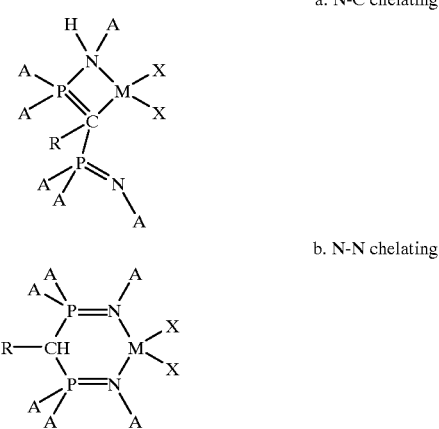

a. N-C chelating b. N-N chelating

The products contain alkyl bridges between the phosphinimine groups. Further, none of the references teach or suggest the use of such compounds for the polymerization of alpha olefins.

U.S. Pat. No. 5,557,023 issued September, 1966 teaches the use of some phosphinimines complexes to oligomerize alpha olefins. Rather, the complexes are of the structure indicated below.

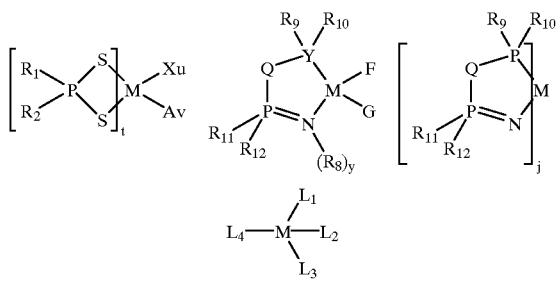

wherein R, Q, etc. are as defined in the patent. The structures disclosed in the patent are not the bisphosphinimines of the present invention. While the reference does teach oligomerization, it does not suggest polymerization.

There are a number of patents and papers by Brookhart and/or Gibson disclosing the use of Group 8, 9 or 10 metals to polymerize olefins. However, such papers teach that copolymers are not produced (e.g. WO 98/27124). The present invention proved copolymers of olefins made using a catalyst of a Group 8, 9 or 10 metal other than nickel.

A poster presentation by Christopher M. Ong and Professor D. W. Stephan at the Chemical Institute of Canada's annual meeting in the summer of 1999 discloses phosphinimine complexes of aluminum. One of the complexes disclosed is similar to those of the present invention except that the metal is aluminum rather than a Group 8, 9 or 10 metal other than nickel. As far as Applicants are aware the poster did not disclose the use of such complexes for the polymerization of olefins.

Lecture 60 from the summer ACS meeting discloses a cubic cobalt complex of phosphinimines. The reference does not disclose olefin polymerization using such complexes. The paper "Phosphiniminato-Cluster von Eisen. Die Kristallstrukturen von $[FeCl(NPEt_3)]_4$, $[FeC|C-SiMe_3)(NPEt_3)]_4$ and $[Fe_3Cl_4[NP(NMe_2)_3]_5]$" also discloses cubic phosphinimine complexes but does not teach their use as olefin polymerization catalysts.

SUMMARY OF THE INVENTION

A process for the polymerization of one or more $C_{2-12}$ alpha olefins in the presence of an activated complex selected from the group consisting of complexes of formula I:

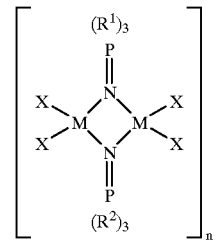

wherein M is a Group 8, 9 or 10 metal other than nickel; each $R^1$ and $R^2$ are independently selected from the group consisting of a hydrocarbyl radical having up to 20 carbon atoms; each X is independently selected from the group consisting of an activatable ligand and n is 1 or 2 provided that if n is 2 and $R^1$ and $R^2$ are not branched, cyclic or aromatic radicals, the complex may be cubic; and complexes of formula II:

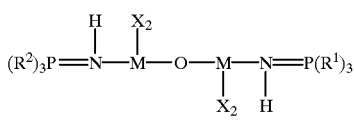

wherein M, $R^1$, $R^2$ and X are as defined above, and an activator.

A further aspect of the present invention provides a complex of formula II:

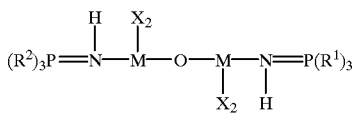

wherein each $R^1$ and $R^2$ are independently selected from the group consisting of a hydrocarbyl radical having up to 20 carbon atoms; each X is independently selected from the group consisting of an activatable ligand.

In a further aspect, the present invention provides a complex of formula I:

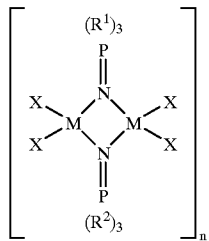

wherein M is a Group 8, 9 or 10 metal other than nickel; $R^1$ and $R^2$ are independently selected from the group consisting of a hydrocarbyl radical having up to 20 carbon atoms; each X is independently selected from the group consisting of an activatable ligand and n is 1 or 2 provided that if n is 2 and $R^1$ and $R^2$ are not branched, cyclic or aromatic radicals, the complex may be cubic and if the complex is cubic M can not be Co or Fe.

DETAILED DESCRIPTION

The term "scavenger" as used in this specification is meant to include those compounds effective for removing polar impurities from the reaction solvent. Such impurities can be inadvertently introduced with any of the polymerization reaction components, particularly with solvent, monomer and catalyst feed; and can adversely affect catalyst activity and stability. It can result in decreasing or even elimination of catalytic activity, particularly when an activator capable of ionizing the iron complex is also present.

As used herein the term "cubic" when applied to the complex means the central structure in the complex is a cube with alternating "M" and nitrogen atoms at the comers of the cube.

When the above complexes are linear M is a Group 8, 9 or 10 metal other than nickel, preferably Fe, Co, Pd or Pt and most preferably Fe. If the complexes are cubic, M may not be Fe or Co, preferably Pd or Pt.

In the above complexes $R^1$ and $R^2$ are independently selected from the group consisting of a hydrocarbyl radical having up to 20 carbon atoms; and each X is independently selected from the group consisting of an activatable ligand. In the complex of formula I, n is 1 or 2 provided that if n is 2 and $R^1$ and $R^2$ are not branched, cyclic or aromatic, the complex may be cubic. Preferably, in the above complexes $R^1$ and $R^2$ are independently selected from the group consisting of $C_{3-10}$ branched or straight chained alkyl radicals and $C_{6-10}$ cyclic alkyl radicals and $C_{6-10}$ aryl radicals. Most preferably $R^1$ and $R^2$ are independently selected from the group consisting of $C_{1-4}$ straight chained or branched alkyl radicals. In a particularly preferred embodiment of the present invention, $R^1$ and $R^2$ are the same and most preferably a t-butyl radical. In the complexes of the present invention each X is independently an activatable ligand. Generally, X may be selected from the group consisting of a halogen atom, $C_{1-10}$ alkyl or alkoxide radicals, $C_{6-10}$ cyclic alkyl radicals, cyclic alkoxide radicals, aryl radicals and aryl oxide radicals. Preferably, X is independently selected form the group consisting of a chlorine atom, a bromine atom, a $C_{1-4}$ alkyl radical and a $C_{1-4}$ alkoxy radical. Suitable alkyl and alkoxy radicals include a methyl radical, an ethyl radical and an ethoxy radical. In some cases it is advantageous if each X is the same.

The metal complexes of the present invention may be prepared by reacting the phosphinimine ligand with a compound such as butyl lithium in an inert hydrocarbyl solvent or diluent. The resulting lithiated ligand may then be reacted with a precursor compound containing M, where M is as defined above, to form the complex. Generally the above reactions may be conducted at temperatures from about –30° C. up to the degradation temperature of the phosphinimine, preferably less than 100° C., most preferably from about 20° C. to about 80° C. For the complex of formula I wherein n is 1 the molar ratio of lithiated phosphinimine ligand to M (Group 8, 9 or 10 metal other than nickel) is from about 1.90 to 2.10, preferably from about 1.92 to 2.05. For the complex of formula 1 wherein n is 2 the molar ratio of lithiated phosphinimine ligand to M, where M is defined above, is from about 3.90 to 4.10, preferably from 3.95 to 4.05. Alternately, to prepare the dimer form (e.g. formula I wherein n is 2). It should be noted that if $R^1$ and $R^2$ are straight chained alkyl groups particularly having less than four carbon atoms, the resulting complex may be cubic. However, if $R^1$ and $R^2$ are not linear, the complex will be linear (i.e. not cubic with nitrogen and M at alternating comers). It is possible to condense two moles of compound of formula I to a mole of compound of formula II. This may be done by reflux or other suitable means.

The complex of formula II in the present invention is prepared by the hydrolysis of the compounds of formula I. This may be accomplished by routine methods known to those skilled in the art. Preferably the complex of formula I is treated under mild conditions, either acid or alkali to hydrolyze the compound.

Solution polymerization processes are fairly well known in the art. These processes are conducted in the presence of an inert hydrocarbon solvent, typically a $C_{5-12}$ hydrocarbon which may be unsubstituted or substituted by a $C_{1-4}$ alkyl group such as pentane, hexane, heptane, octane, cyclohexane, methylcyclohexane or hydrogenated naphtha. An additional solvent is Isopar E ($C_{8-12}$ aliphatic solvent, Exxon Chemical Co.).

The polymerization may be conducted at temperatures from about 20° C. to about 250° C. Depending on the product being made, this temperature may be relatively low such as from 20° C. to about 120° C. for a slurry process and from 120° C. to 250° C. for the solution process. The pressure of the reaction may be as high as about 15,000 psig for the older high pressure processes or may range from about 15 to 4,500 psig.

Suitable olefin monomers may be ethylene and $C_{3-20}$ mono- and di-olefins. Preferred monomers include ethylene and $C_{3-12}$ alpha olefins which are unsubstituted or substituted by up to two $C_{1-6}$ alkyl radicals. Illustrative non-limiting examples of such alpha olefins are one or more of propylene, 1-butene, 1-pentene, 1-hexene, 1-octene and 1-decene.

The reaction product of the present invention, in the presence of a single alpha olefin, may be an oligomer having a molecular weight (Mw) less than about 1500. The reaction product of the present invention may also be a co- or homopolymer of one or more alpha olefins. The polymers prepared in accordance with the present invention have a good molecular weight. That is, weight average molecular weight (Mw) will preferably be greater than about 50,000 ranging up to $10^7$, preferably $10^5$ to $10^6$.

The polyethylene polymers which may be prepared in accordance with the present invention typically comprise not less than 60, preferably not less than 70, most preferably not less than 80 weight % of ethylene and the balance of one or more $C_{4-10}$ alpha olefins, preferably selected from the group consisting of 1-butene, 1-hexene and 1-octene. The polyethylene prepared in accordance with the present invention may contain branching (e.g. one or more branches per 1000 carbon atoms, preferably 1–30 branches per 1000 carbon atoms, typical 1–20 branches per 1000 carbon atoms and most preferably 1–10 branches per 1000 carbon atoms).

The activator may be selected from the group consisting of:

(i) an aluminoxane; and (ii) an activator capable of ionizing the Group 8, 9 or 10 metal complex (which may be used in combination with an alkylating activator). The aluminoxane activator may be of the formula $(R^{20})_2AlO(R^{20}AlO)_mAl(R^{20})_2$ wherein each $R^{20}$ is independently selected from the group consisting of $C_{1-20}$ hydrocarbyl radicals, m is from 0 to 50, and preferably $R^{20}$ is a $C_{1-4}$ alkyl radical and m is from 5 to 30. The aluminoxane activator may be used prior to the reaction but preferably in situ alkylation is typical (e.g. alkyl groups replacing leaving ligands, hydrogen or halide groups).

If the Group 8, 9 or 10 metal complex is activated only with aluminoxane, the amount of aluminoxane will depend on the reactivity of the alkylating agent. Activation with aluminoxane generally requires a molar ratio of aluminum in the activator to the Group 8, 9 or 10 metal other than nickel in the complex may range from 50:1 to 1000:1.

The activator of the present invention may be a combination of an alkylating activator which also serves as a scavenger other than aluminoxane in combination with an activator capable of ionizing the Group 8, 9 or 10 metal other than nickel in the complex.

The alkylating activator (which may also serve as a scavenger) may be selected from the group consisting of: $(R)_pMgX_{2-p}$ wherein X is a halide, each R is independently selected from the group consisting of $C_{1-10}$ alkyl radicals, preferably $C_{1-8}$ alkyl radicals and p is 1 or 2; RLi wherein R is as defined above; $(R)_qZnX_{2-q}$ wherein R is as defined above, X is halogen and q is 1 or 2; $(R)_sAlX_{3-s}$ wherein R is as defined above, X is halogen and s is an integer from 1 to 3. Preferably in the above compounds R is a $C_{1-4}$ alkyl radical and X is chlorine. Commercially available compounds include triethyl aluminum (TEAL), diethyl aluminum chloride (DEAC), dibutyl magnesium ($(Bu)_2Mg$) and butyl ethyl magnesium (BuEtMg or BuMgEt).

The activator capable of ionizing the Group 8, 9 or 10 metal other than nickel in the complex may be selected from the group consisting of:

(i) compounds of the formula $[R^{15}]^+[B(R^{18})_4]^-$ wherein B is a boron atom, $R^{15}$ is a cyclic $C_{5-7}$ aromatic cation or a triphenyl methyl cation and each $R^{18}$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom; and a silyl radical of the formula $-Si-(R^{19})_3$ wherein each $R^{19}$ is independently selected from the group consisting of a hydrogen atom and a $C_{1-4}$ alkyl radical; and (ii) compounds of the formula $[(R^{16})_tZH]^+[B(R^{18})_4]^-$ wherein B is a boron atom, H is a hydrogen atom, Z is a nitrogen atom or phosphorus atom, t is 2 or 3 and $R^16$ is selected from the group consisting of $C_{1-8}$ alkyl radicals, a phenyl radical which is unsubstituted or substituted by up to three $C_{1-4}$ alkyl radicals, or one $R^{16}$ taken together with the nitrogen atom to form an anilinium radical and $R^{18}$ is as defined above; and iii) compounds (activators) of the formula $B(R^{18})_3$ wherein $R^{18}$ is as defined above.

In the above compounds preferably $R^{18}$ is a pentafluorophenyl radical, $R^{15}$ is a triphenylmethyl cation, Z is a nitrogen atom and $R^{16}$ is a $C_{1-4}$ alkyl radical or $R^{16}$ taken together with the nitrogen atom forms an anilium radical which is substituted by two $C_{1-4}$ alkyl radicals.

The activator capable of ionizing the Group 8, 9 or 10 metal other than nickel in the complex abstracts one or more X ligands so as to ionize the metal into a cation, but not to covalently bond with the metal and to provide sufficient distance between the ionized metal and the ionizing activator to permit a polymerizable olefin to enter the resulting active site.

Examples of compounds capable of ionizing the Group 8, 9 or 10 metal other than nickel complex include the following compounds:

triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tributylammonium tetra(pentafluorophenyl)boron,
tri(n-butyl)ammonium tetra(o-tolyl)boron,
N,N-dimethylanilinium tetra(phenyl)boron,
N,N-diethylanilinium tetra(phenyl)boron,
N,N-diethylanilinium tetra(phenyl)n-butylboron,
N,N-2,4,6-pentamethylanilinium tetra(phenyl)boron
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate, triphenylmethylium tetrakis (1,2,2-trifluoroethenyl) borate, benzene (diazonium) tetrakis (1,2,2-trifluoroethenyl) borate, tropillium tetrakis (2,3,4,5-tetrafluorophenyl) borate, triphenylmethylium tetrakis (2,3,4,5-tetrafluorophenyl) borate, and benzene (diazonium) tetrakis (2,3,4,5-tetrafluorophenyl) borate.

Readily commercially available activators which are capable of ionizing the complexes of the present invention include:

N,N-dimethylaniliniumtetrakispentafluorophenyl borate, triphenylmethylium tetrakispentafluorophenyl borate, and trispentafluorophenyl boron.

If the complex is activated with a combination of an aluminum alkyl compound (generally other than aluminoxane), and a compound capable of ionizing the Group 8, 9 or 10 metal other than nickel complex (e.g. activators (I) and (III) above) the molar ratios of Group 8, 9 or 10 metal other than nickel:metal in the alkylating agent (e.g. Al); metalloid (e.g. boron or phosphorus) in the activator capable of ionizing the complex (e.g. boron) may range from 1:1:1 to 1:100:5. Preferably, the alkylating activator is premixed/reacted with the complex and the resulting alkylated species is then reacted with the activator capable of ionizing the Group 8, 9 or 10 metal other than nickel.

In a solution polymerization the monomers are dissolved/dispersed in the solvent either prior to being fed to the reactor, or for gaseous monomers, the monomer may be fed to the reactor so that it will dissolve in the reaction mixture. Prior to mixing, the solvent and monomers are generally purified to remove polar moieties. The polar moieties or catalyst poisons include water, oxygen, metal impurities, etc. Preferably steps are taken before provision of such into the reaction vessel, for example by chemical treatment or careful separation techniques after or during the synthesis or preparation of the various components. The feedstock purification prior to introduction into the reaction solvent follows standard practices in the art (e.g. molecular sieves, alumina beds and oxygen removal catalysts) are used for the purification of ethylene, alpha-olefin and optional diene. The solvent itself as well (e.g. cyclohexane and toluene) is similarly treated. In some instances, out of an abundance of caution, excess scavenging activators may be used in the polymerization process.

The feedstock may be heated prior to feeding into the reactor. However, in many instances it is desired to remove heat from the reactor so the feedstock may be at ambient temperature to help cool the reactor.

Generally, the catalyst components may be premixed in the solvent for the reaction or fed as separate streams to the reactor. In some instances premixing is desirable to provide a reaction time for the catalyst components prior to entering the reaction. Such an "in line mixing" technique is described in a number of patents in the name of DuPont Canada Inc. For example, it is described in U.S. Pat. No. 5,589,555 issued Dec. 31, 1996.

The reactor may comprise a tube or serpentine reactor used in the "high pressure" polymerizations or it may comprise one or more reactors or autoclaves. It is well known to use two such reactors in series, each of which may be operated independently to achieve different polymer molecular weight distributions. The residence time in the reactor system will depend on the design and the capacity of the reactor. Generally, the reactors should be operated under conditions to achieve a thorough mixing of the reactants. On leaving the reactor system the solvent is removed and the resulting polymer is finished in a conventional manner.

The present invention will now be illustrated by the following examples in which unless otherwise specified weight means weight % and parts means parts by weight (e.g. grams).

EXAMPLE 1

Preparation of $[(^tBu_3P=N)FeBr_2]_n$ (n likely=2) (1)

To a solution (10 mL) of $^tBu_3P=NH$ (283 mg, 1.30 mmol) in toluene was added slowly $^nBuLi$ in hexane (1.6 M, 0.81 mL, 1.3 mmol). The solution was stirred at room temperature for 20 minutes. The above solution was then added slowly to a toluene solution (40 mL) of $FeBr_3$ (385 mg, 1.3 mmol) at −30° C. The mixture was slowly warmed to room temperature and was stirred for 12 hours. A brownish orange solution formed. The solution was filtered to remove LiBr and the filtrate was concentrated and mixed with heptane. The product crystallized at −35° C. to give an orange crystalline material (540 mg, 96%).

EXAMPLE 2

$(^tBu_3P=NH)Br_2FeOFeBr_2(HN=P^tBu_3)$ (2)

$^tBu_3P=NH$ (0.217 g, 1.0 mmol) was dissolved in anhydrous heptane. With stirring, a 0.63 mL volume of 1.6 M $^nBuLi$ was added dropwise. The reaction mixture was allowed to stir at room temperature for one hour and was used in situ for the next step. $FeBr_3$ (0.296 g, 1.0 mmol, Note: this commercial product from Aldrich was not dry enough) was dissolved in 30 mL anhydrous toluene. The red colored solution was cooled to −100° C., and the slurry of lithiated $^tBu_3P=NH$ initially prepared above, was added with stirring. After the addition was complete, the reaction mixture was warmed to room temperature, at which point the solution became brown in color (with a slight green tinge) and solid was observed. The mixture was allowed to stir overnight under $N_2$. Solid LiCl was removed by filtration and the solvent was removed under vacuum. The product was a dark green oily solid which was subsequently purified by rinsing with heptane. The final product was a light green powder. Yield was 34% (0.150 g, 0.347 mmol). The product was identified by single X-ray crystallography as $(^tBu_3P=NH)Br_2FeOFeBr_2(HN=P^tBu_3)$.

EXAMPLE 3

Hydrolysis of the Product (3)

In another experiment, starting with $^tBu_3P=NH$ (406 mg, 1.867 mmol), $^nBuLi$ (1.6 M, 1.16 mL), $FeBr_3$ (552 mg, 1.86 mmol, good quality) the same procedures were followed as the above example 2. A brownish orange solution was obtained. To this solution $H_2O$ (5 mg, 0.27 mmol) in toluene (60 mL) was added dropwise. The solution turned to brownish green and was further stirred for 12 hours. The resultant solution was filtered and the filtrate was pumped to dryness to give a greenish solid.

This solid was used as is for polymerization example.

EXAMPLE 4

Preparation of $[(^tBu_3P=N)FeCl_2]_n$ (4)

$^tBu_3P=NLi$ (0.223 g, 1 mmol) in toluene (~10 mL) was added to a toluene solution (~20 mL) of $FeCl_3$ (162 mg, 1 mmol) at −100° C. The mixture was warmed to room temperature and was stirred overnight. A dark green slurry formed which was then filtered. The green solid produced was washed with heptane and then dried. The filtrate was concentrated to a couple of milliliters by vacuum pumping and was stored at −70° C. overnight. Dark crystals formed which were separated from the mother liquor, washed with heptane and dried. The combined yield was 180 mg (53%).

Polymerization Results

In the examples, the pressures given are gauge pressures. The following abbreviations and terms are used:

Polydispersity: weight average molecular weight (Mw) divided by number average molecular weight (Mn).

DSC: differential scanning calorimetry.

GPC: gel permeation chromatography.

MeOH: methanol.

PMAO-IP: a type of polymethylaluminoxane.

m.p.: polymer melting point.

All the polymerization experiments described below were conducted using a 500 mL Autoclave Engineers Zipperclave™ reactor. All the chemicals (solvent, catalyst and cocatalyst) were fed into the reactor batchwise except ethylene which was fed on demand. No product was removed during the polymerization reaction. As known to those skilled in the art, all the feed streams were purified prior to feeding into the reactor by contact with various absorption media to remove catalyst killing impurities such as water, oxygen, sulfur and polar materials. All components were stored and manipulated under an atmosphere of purified argon or nitrogen. The reactor uses a programmable logic control (PLC) system with WONDERWARE™ 5.1 software for the process control. Ethylene polymerization experiments were performed in the reactor which was equipped with an air driven stirrer and an automatic temperature control system.

Polymerization temperature setting was 50° C. for slurry polymerization runs and 160° C. for solution polymerization runs. The polymerization reaction time varied from 8 to 30 minutes for each experiment. The reaction was terminated by adding 5 mL of methanol to the reactor and the polymer was recovered by evaporation of the toluene. The polymerization activities were calculated based on the weight of the polymers produced.

The catalysts (Fe catalyst 1–4) were dissolved in toluene. The anhydrous toluene was purchased from Aldrich and purified over molsieves prior to use. PMAO-IP was purchased from Akzo-Nobel and contained 13.5 weight % of Al. [CPh$_3$][B(C$_6$F$_5$)$_4$] (hereinafter trityl borate) was purchased from Asahi Glass Inc.; lot #: 980224.

Polymer molecular weights and molecular weight distributions were measured by GPC (WATERS™ 150-C) at 140° C. in 1,2,4-trichlorobenzene calibrated using polyethylene standards.

DSC was conducted on a DSC 220 from SEIKO™ Instruments. The heating rate is 10° C./minute from 0 to 200° C.

NMR (BRUCK™-300-DPS, 125° C. in trichloroethane-d$_3$] was used to determine the branching per 1000 carbon atoms.

Slurry Polymerizations

TABLE 1

| | Polymerization Data[1] | | |
|---|---|---|---|
| Catalyst/Cocatalyst | Average Run Temperature (° C.) | Run Time (min.) | Polymerization Activity (g polymer/mmolFe*hr) |
| Fe catalyst 1/PMAO-IP/trityl borate[2] | 83.1 | 24 | 1121.0 |
| Fe catalyst 1/PMAO-IP[3] | 51.2 | 15 | 30.8 |
| Fe catalyst 2/PMAO-IP | 65.9 | 30 | 643.6 |
| Fe catalyst 3/PMAO-IP | 50.0 | 8 | 1316.1 |
| Fe catalyst 3/PMAO-IP[3] | 50.0 | 30 | 21.5 |
| Fe catalyst 4/PMAO-IP | 51.5 | 30 | 34.0 |

[1]General homopolymerization conditions: 50° C. as a setting temperature; 300 psig of C2; 300 umol/L of catalyst concentration; PMAO-IP as a cocatalyst with Al/Fe = 60; 216 mL of toluene as solvent.
[2]In-situ alkylation plus trityl borate activation 50° C. as a setting temperature; 300 psig of C2; 300 umol/L of catalyst concentration; PMAO-IP as an alkylation reagent with Al/Fe = 20; trityl borate as cocatalyst at B/Al = 1.05; PMAO-IP at 1 mmol/L as a scavenger; 216 mL of toluene as solvent.
[3]Copolymerization conditions: 50° C. as a setting temperature; 100 psig of C2; 300 umol/L of catalyst concentration; PMAO-IP as a cocatalyst with Al/Fe = 60; 30 mL of 1-octene; 216 mL of toluene as solvent.

TABLE 2

| | Polymer Property Data | | |
|---|---|---|---|
| Catalyst/Cocatalyst | Mw(*10$^{-3}$) | Pd | m.p. |
| Fe catalyst 1/PMAO-IP/trityl borate | 139.6 | 1.7 | 136.2 |
| Fe catalyst 1/PMAO-IP[2] | 509.9 | 7.0 | 106.7 |
| Fe catalyst 2/PMAO-IP | 120.0 | 44.7 | 127.5 |
| Fe catalyst 3/PMAO-IP | 149.5 | 50.7 | 132.0 |
| Fe catalyst 3/PMAO-IP[2] | 468.8 | 16.7 | 125.3 |
| Fe catalyst 4/PMAO-IP | 480.3 | 11.3 | 132.1 |

[1]General homopolymerization conditions: 50° C. as a setting temperature; 300 psig of C2; 300 umol/L of catalyst concentration; PMAO-IP as a cocatalyst with Al/Fe = 60; 216 mL of toluene as solvent.
[2]In-situ alkylation plus trityl borate activation: 50° C. as a setting temperature; 300 psig of C2; 300 umol/L of catalyst concentration; PMAO-IP as an alkylation reagent with Al/Fe = 20; trityl borate as cocatalyst at B/Al = 1.05; PMAO-IP at 1 mmol/L as a scavenger; 216 mL of toluene as solvent.
[3]Copolymerization conditions: 50° C. as a setting temperature; 100 psig of C2; 300 umol/L of catalyst concentration; PMAO-IP as a cocatalyst with Al/Fe = 60; 30 mL of 1-octene; 216 mL of toluene as solvent.

TABLE 3

| | Polymerization Data[1] | | |
|---|---|---|---|
| Catalyst/Cocatalyst | Average Run Temperature (° C.) | Run Time (min.) | Polymerization Activity (g polymer/mmol Fe*hr) |
| Fe catalyst 1/PMAO-IP/trityl borate | 158.5 | 10 | 654.9 |
| Fe catalyst 3/PMAO-IP/tritylborate | 159.2 | 10 | 177.8 |

[1]General polymerization conditions: in-situ alkylation plus trityl borate activation: 160° C. as a setting temperature; 200 psig of C2; 200 umol/L of catalyst concentration; PMAO-IP as an alkylation reagent with Al/Fe = 20; trityl borate as cocatalyst at B/Al = 1.05; PMAO-IP at 1 mmol/L as a scavenger; 216 mL of toluene as solvent.

TABLE 4

Polymer Property Data[1]

| Catalyst/Cocatalyst | Mw(*10$^{-3}$) | Pd | m.p. |
|---|---|---|---|
| Fe catalyst 1/PMAO-IP/trityl borate | 451.1 | 1.82 | 133.9 |
| Fe catalyst 3/PMAO-IP/tritylborate | 547.1 | 1.71 | 141.5 |

[1]General polymerization conditions: in-situ alkylation plus trityl borate activation: 160° C. as a setting temperature; 200 psig of C2; 200 umol/L of catalyst concentration; PMAO-IP as an alkylation reagent with Al/Fe = 20; trityl borate as cocatalyst at B/Al = 1.05; PMAO-IP at 1 mmol/L as a scavenger; 216 mL of toluene as solvent.

What is claimed is:

1. A process for the polymerization of one or more $C_{2-12}$ alpha olefins in the presence of an activated complex selected from the group consisting of complexes of formula I:

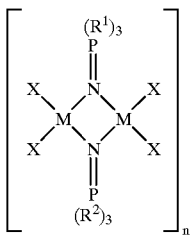

wherein M is a Group 8, 9 or 10 metal other than nickel; each $R^1$ and $R^2$ are independently selected from the group consisting of a hydrocarbyl radical having up to 20 carbon atoms; each X is independently selected from the group consisting of an activatable ligand and n is 1 or 2 provided that if n is 2 and $R^1$ and $R^2$ are not branched, cyclic or aromatic radicals, the complex may be cubic; and complexes of formula II:

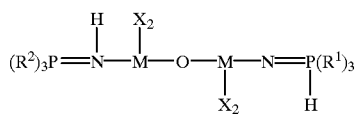

wherein M, $R^1$, $R^2$ and X are as defined above, and an activator.

2. The process according to claim 1, wherein the activator is selected from the group consisting of:
   (i) an aluminum compound selected from the group consisting of aluminum alkyls of the formula $AlR_{3-n}X_n$ in which R is independently selected from the group consisting of a $C_{1-8}$ alkyl radical, X is a halogen atom and n is 0, 1, 2 or 3 to provide a mole ratio of aluminum to M of at least 5:1;
   (ii) aluminoxane compounds $R^{20}{}_2AlO(R^{20}AlO)_mAlR^{20}{}_2$ wherein each $R^{20}$ is independently selected from the group consisting of $C_{1-20}$ hydrocarbyl radical and m is from 5 to 30 to provide a molar ratio of aluminum to M from 50:1 to 1000:1;
   (iii) anions of the formula $[B(R^{18})_4]^-$ wherein each $R^{18}$ is independently selected from the group consisting of phenyl radicals which are unsubstituted or substituted by up to 5 substituents selected from the group consisting of a fluorine atom, a $C_{1-4}$ alkyl or alkoxy radical which is unsubstituted or substituted by a fluorine atom and a silyl radical of the formula $-Si-(R^{19})_3$; wherein each $R^{19}$ is independently selected from the group consisting of a hydrogen atom and a $C_{1-4}$ alkyl radical; and an activator of the formula $[B(R^{18})_3]$ wherein $R^{18}$ is as defined above and to provide a molar ratio of M to boron from 1:1 to 1:3; and
   (iv) a mixture of activators (i) and (iii) to provide a ratio of M to aluminum to boron from 1:1:1 to 1:100:5.

3. The process according to claim 2, wherein said one or more olefins are selected from the group consisting of ethylene, propylene, butylene, hexene and octene.

4. The process according to claim 3, wherein M is selected from the group consisting of Fe, Co, Pd or Pt.

5. The process according to claim 4, wherein in the complex, each X is selected from the group consisting of a halide atom or a $C_{1-10}$ alkyl or alkoxide radical, and a $C_{6-10}$ cyclic alkyl, alkoxide, aryl and aryloxide radical.

6. The process according to claim 5, wherein in the complex, each of $R^1$ and $R^2$ is independently selected from the group consisting of $C_{3-10}$ branched or straight chained alkyl radicals and $C_{6-10}$ cyclic alkyl radicals and aryl radicals.

7. The process according to claim 6, wherein in the complex, all the $R^1$ and $R^2$ radicals are the same.

8. The process according to claim 7, wherein in the complex of formula I, each X is independently selected from the group consisting of a chloride atom, a bromine atom, a $C_{1-4}$ alkyl radical and a $C_{1-4}$ alkoxy radical.

9. The process according to claim 8, wherein in the complex of formula I, each X is independently selected from the group consisting of a chlorine atom, a bromine atom, a methyl radical, a methoxy radical, an ethyl radical and an ethoxy radical.

10. The process according to claim 9, wherein in the complex is formula I and n is 1.

11. The process according to claim 10, wherein the temperature is from 120° C. to 250° C., the pressure is from 100 to 4,500 psig and the activator is an aluminoxane in which each $R^{20}$ is selected from the group consisting of $C_{1-4}$ alkyl radicals and m is from 5 to 30.

12. The process according to claim 10, wherein the temperature is from 20° C. to 120° C., the pressure is from 100 to 4,500 psig and the activator is an aluminoxane in which each $R^{20}$ is selected from the group consisting of $C_{1-4}$ alkyl radicals and m is from 5 to 30.

13. The process according to claim 10, wherein the temperature is from 120° C. to 250° C., the pressure is from 100 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

14. The process according to claim 10, wherein the temperature is from 20° C. to 120° C., the pressure is from 15 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

15. The process according to claim 10, wherein the temperature is from 120° C. to 250° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

16. The process according to claim 10, wherein the temperature is from 20° C. to 120° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

17. The process according to claim 11, wherein M is Fe, X is a chlorine atom and $R^1$ and $R^2$ are tert-butyl radicals.

18. The process according to claim 12, wherein M is Fe, X is a chlorine atom and $R^1$ and $R^2$ are tert-butyl radicals.

19. The process according to claim 13, wherein M is Fe, X is a chlorine atom and $R^1$ and $R^2$ are tert-butyl radicals.

20. The process according to claim 14, wherein M is Fe, X is chlorine atom and $R^1$ and $R^2$ are tert-butyl radicals.

21. The process according to claim 15, wherein M is Fe, X is a chlorine atom and $R^1$ and $R^2$ are tert-butyl radicals.

22. The process according to claim 16, wherein M is Fe, X is a chlorine atom and $R^1$ and $R^2$ are tert-butyl radicals.

23. The process according to claim 9, wherein in the complex is formula I and n is 2.

24. The process according to claim 23, wherein in the complex of formula I, each of $R^1$ and $R^2$ is independently selected from the group consisting of $C_{3-10}$ straight chained alkyl radicals.

25. The process according to claim 24, wherein the complex of formula I is linear.

26. The process according to claim 25, wherein the temperature is from 120° C. to 250° C., the pressure is from 100 to 4,500 psig and the activator is an aluminoxane in which each $R^{20}$ is selected from the group consisting of $C_{1-4}$ alkyl radicals and m is from 5 to 30.

27. The process according to claim 25, wherein the temperature is from 20° C. to 120° C., the pressure is from 100 to 4,500 psig and the activator is an aluminoxane in which each $R^{20}$ is selected from the group consisting of $C_{1-4}$ alkyl radicals and m is from 5 to 30.

28. The process according to claim 25, wherein the temperature is from 120° C. to 250° C., the pressure is from 100 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

29. The process according to claim 25, wherein the temperature is from 20° C. to 120° C., the pressure is from 15 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

30. The process according to claim 25, wherein the temperature is from 120° C. to 250° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

31. The process according to claim 25, wherein the temperature is from 20° C. to 120° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

32. The process according to claim 26, wherein M is Fe and X is a chlorine atom.

33. The process according to claim 27, wherein M is Fe and X is a chlorine atom.

34. The process according to claim 28, wherein M is Fe and X is a chlorine atom.

35. The process according to claim 29, wherein M is Fe and X is a chlorine atom.

36. The process according to claim 30, wherein M is Fe and X is a chlorine atom.

37. The process according to claim 31, wherein M is Fe and X is a chlorine atom.

38. The process according to claim 23, wherein the complex of formula I is cubic.

39. The process according to claim 38, wherein $R^1$ and $R^2$ are selected from the group consisting of $C_{3-10}$ branched alkyl radicals and $C_{6-10}$ cyclic alkyl radicals and aryl radicals.

40. The process according to claim 39, wherein the temperature is from 120° C. to 250° C., the pressure is from 100 to 4,500 psig and the activator is an aluminoxane in which each $R^{20}$ is selected from the group consisting of $C_{1-4}$ alkyl radicals and m is from 5 to 30.

41. The process according to claim 39, wherein the temperature is from 20° C. to 120° C., the pressure is from 100 to 4,500 psig and the activator is an aluminoxane in which each $R^{20}$ is selected from the group consisting of $C_{1-4}$ alkyl radicals and m is from 5 to 30.

42. The process according to claim 39, wherein the temperature is from 120° C. to 250° C., the pressure is from 100 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

43. The process according to claim 39, wherein the temperature is from 20° C. to 120° C., the pressure is from 15 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

44. The process according to claim 39, wherein the temperature is from 120° C. to 250° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

45. The process according to claim 39, wherein the temperature is from 20° C. to 120° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

46. The process according to claim 40, wherein M is Fe, X is a chlorine atom and $R^1$ and $R^2$ are tertiary butyl radicals.

47. The process according to claim 41, wherein M is Fe, X is a chlorine atom and $R^1$ and $R^2$ are tertiary butyl radicals.

48. The process according to claim 42, wherein M is Fe, X is chlorine atom and $R^1$ and $R^2$ are tertiary butyl radicals.

49. The process according to claim 43, wherein M is Fe, X is chlorine atom and $R^1$ and $R^2$ are tertiary butyl radicals.

50. The process according to claim 44, wherein M is Fe, X is chlorine atom and $R^1$ and $R^2$ are tertiary butyl radicals.

51. The process according to claim 45, wherein M is Fe, X is chlorine atom and $R^1$ and $R^2$ are tertiary butyl radicals.

52. The process according to claim 9, wherein in the complex is of formula II.

53. The process according to claim 52, wherein the temperature is from 120° C. to 250° C., the pressure is from 100 to 4,500 psig and the activator is an aluminoxane in which each $R^{20}$ is selected from the group consisting of $C_{1-4}$ alkyl radicals and m is from 5 to 30.

54. The process according to claim 52, wherein the temperature is from 20° C. to 120° C., the pressure is from 100 to 4,500 psig an d the activator is an aluminoxane in which each $R^{20}$ is selected from the group consisting of $C_{1-4}$ alkyl radicals and m is from 5 to 30.

55. The process according to claim 52, wherein the temperature is from 120° C. to 250° C., the pressure is from 100 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

56. The process according to claim 52, wherein the temperature is from 20° C. to 120° C., the pressure is from 15 to 4,500 psig and the activator is an ionic activator selected from the group consisting of N,N-dimethylaniliniumtetrakispentafluorophenyl borate, triphenylmethylium tetrakispentafluorophenyl borate and trispentafluorophenyl boron.

57. The process according to claim 52, wherein the temperature is from 120° C. to 250° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

58. The process according to claim 52, wherein the temperature is from 20° C. to 120° C., the pressure is from 15 to 4,500 psig and the activator is a combination of an ionic activator selected from the group consisting of N,N-dimethylaniliniumtetrakispentafluorophenyl borate, triphenylmethylium tetrakispentafluorophenyl borate and trispentafluorophenyl boron and an aluminum alkyl compound.

59. The process according to claim 53, wherein M is Fe, X is a chlorine atom and $R^1$ and $R^2$ are tertiary butyl radicals.

60. The process according to claim 54, wherein M is Fe, X is a chlorine atom and $R^1$ and $R^2$ are tertiary butyl radicals.

61. The process according to claim 55, wherein M is Fe, X is chlorine atom and $R^1$ and $R^2$ are tertiary butyl radicals.

62. The process according to claim 56, wherein M is Fe, X is chlorine atom and $R^1$ and $R^2$ are tertiary butyl radicals.

63. The process according to claim 57, wherein M is Fe, X is chlorine atom and $R^1$ and $R^2$ are tertiary butyl radicals.

64. The process according to claim 58, wherein M is Fe, X is chlorine atom and $R^1$ and $R^2$ are tertiary butyl radicals.

65. A complex of formula II:

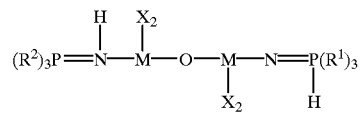

wherein each $R^1$ and $R^2$ are independently selected from the group consisting of a hydrocarbyl radical having up to 20 carbon atoms; each X is independently selected from the group consisting of an activatable ligand.

66. The complex according to claim 65, wherein M is selected from the group consisting of Fe, Co, Pd and Pt.

67. The complex according to claim 66, wherein each X is selected from the group consisting of a halide atom or a $C_{1-10}$ alkyl or alkoxide radical, and a $C_{6-10}$ cyclic alkyl, alkoxide, aryl and aryloxide radical.

68. The complex according to claim 67, wherein each of $R^1$ and $R^2$ is independently selected from the group consisting of $C_{3-10}$ branched or straight chained alkyl radicals and $C_{6-10}$ cyclic alkyl radicals and aryl radicals.

69. The complex according to claim 68, wherein all the $R^1$ and $R^2$ radicals are the same.

70. The complex according to claim 69, wherein each $R^1$ and $R^2$ is a t-butyl radical.

71. The complex according to claim 70, wherein each X is independently selected from the group consisting of a chlorine atom, a bromine atom, a $C_{1-4}$ alkyl radical and a $C_{1-4}$ alkoxy radical.

72. The complex according to claim 71, wherein each X is independently selected from the group consisting of a chlorine atom, a bromine atom, a methyl radical, a methoxy radical, an ethyl radical and an ethoxy radical.

73. The complex according to claim 72, wherein M is Fe.

74. The complex according to claim 73, wherein each X is a chlorine atom.

75. A complex of formula I:

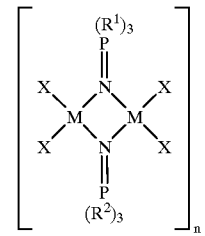

wherein M is a Group 8, 9 or 10 metal other than nickel; $R^1$ and $R^2$ are independently selected from the group consisting of a hydrocarbyl radical having up to 20 carbon atoms; each X is independently selected from the group consisting of an activatable ligand and n is 1 or 2 provided that if n is 2 and $R^1$ and $R^2$ are not branched, cyclic or aromatic radicals, the complex may be cubic and if the complex is cubic M can not be Co or Fe.

76. The complex according to claim 75, wherein M is selected from the group consisting of Fe, Co, Pd or Pt.

77. The complex according to claim 76, wherein each X is selected from the group consisting of a halide atom or a $C_{1-10}$ alkyl or alkoxide radical, and a $C_{6-10}$ cyclic alkyl, alkoxide, aryl and aryloxide radical.

78. The complex according to claim 77, wherein each $R^1$ and $R^2$ is independently selected from the group consisting of $C_{3-10}$ branched or straight chained alkyl radicals and $C_{6-10}$ cyclic alkyl radicals and aryl radicals.

79. The complex according to claim 78, wherein all the $R^1$ and $R^2$ radicals are the same.

80. The complex according to claim 79, wherein each X is independently selected from the group consisting of a chloride atom, a bromine atom, a $C_{1-4}$ alkyl radical and a $C_{1-4}$ alkoxy radical.

81. The complex according to claim 80, wherein each X is independently selected from the group consisting of a chlorine atom, a bromine atom, a methyl radical, a methoxy radical, an ethyl radical and an ethoxy radical.

82. The complex according to claim 81, wherein $R^1$ and $R^2$ are selected from the group consisting of $C_{3-10}$ branched alkyl radicals and $C_{6-10}$ cyclic alkyl radicals and aryl radicals.

83. The complex according to claim 82, wherein each $R^1$ and $R^2$ is a t-butyl radical and M is Fe.

84. The complex according to claim 80, wherein $R^1$ and $R^2$ are selected from the group consisting of $C_{3-10}$ straight chained alkyl radicals.

85. The complex according to claim 84, wherein n is 1.

86. The complex according to claim 84, wherein n is 2.

87. The complex according to claim 86 which is linear.

88. The complex according to claim 86 which is cubic.

\* \* \* \* \*